United States Patent [19]
Legay

[11] Patent Number: 5,935,153
[45] Date of Patent: Aug. 10, 1999

[54] ACTIVE IMPLANTABLE MEDICAL DEVICE ENSLAVED TO A SIGNAL OF ACCELERATION

[75] Inventor: Thierry Legay, Fontenay Les Briis, France

[73] Assignee: ELA Medical S.A., Montrouge, France

[21] Appl. No.: 08/974,444

[22] Filed: Nov. 20, 1997

[30] Foreign Application Priority Data

Nov. 21, 1996 [FR] France .................................. 96 14164

[51] Int. Cl.⁶ .................................................. A61N 1/362
[52] U.S. Cl. ................................................ 607/19; 607/18
[58] Field of Search ........................................ 607/17–19

[56] References Cited

U.S. PATENT DOCUMENTS

| | | |
|---|---|---|
| 3,593,718 | 7/1971 | Kraemer et al. . |
| 4,140,132 | 2/1979 | Dahl . |
| 4,201,219 | 5/1980 | Gonzalez . |
| 4,653,326 | 3/1987 | Danel et al. . |
| 4,771,780 | 9/1988 | Sholder . |
| 4,926,863 | 5/1990 | Alt . |
| 5,012,316 | 4/1991 | Silvermint . |
| 5,014,700 | 5/1991 | Alt . |
| 5,014,702 | 5/1991 | Alt . |
| 5,014,703 | 5/1991 | Alt . |
| 5,014,704 | 5/1991 | Alt . |
| 5,016,632 | 5/1991 | Hoegnelid et al. . |
| 5,031,614 | 7/1991 | Alt . |
| 5,031,615 | 7/1991 | Alt . |
| 5,233,984 | 8/1993 | Thompson . |
| 5,318,596 | 6/1994 | Barreras et al. ........................ 607/19 |
| 5,330,510 | 7/1994 | Legay et al. . |

FOREIGN PATENT DOCUMENTS

| | | |
|---|---|---|
| 259658-A2 | 3/1988 | European Pat. Off. . |
| 259658-A3 | 10/1995 | European Pat. Off. . |
| WO 88/09684 | 12/1988 | WIPO . |
| WO 96/30080 | 10/1996 | WIPO . |

*Primary Examiner*—William E. Kamm
*Assistant Examiner*—Georee R. Evanisko
*Attorney, Agent, or Firm*—Orrick, Herrington & Sutcliffe LLP

[57] ABSTRACT

An active implantable medical device, particularly a cardiac pacemaker, which is enslaved to a signal representative of acceleration, having a measuring circuit (10) comprising at least one sensor (12) delivering a signal of acceleration, and circuits (22–24) to deliver, in response to the signal of acceleration, a parameter of enslavement of at least one function of the device, particularly that of a cardiac stimulation frequency. According to the invention, a circuit (24) operates to limit, in the detection of increase in acceleration, a value linked to the module of the signal of acceleration. Preferably, the limitation is operated on a value proportional to the square of the signal of acceleration, more particularly on a quadratic sum of individual acceleration components $(X_i, Y_i, Z_i)$ according to at least two distinct axes delivered by a respective number of sensors.

19 Claims, 2 Drawing Sheets

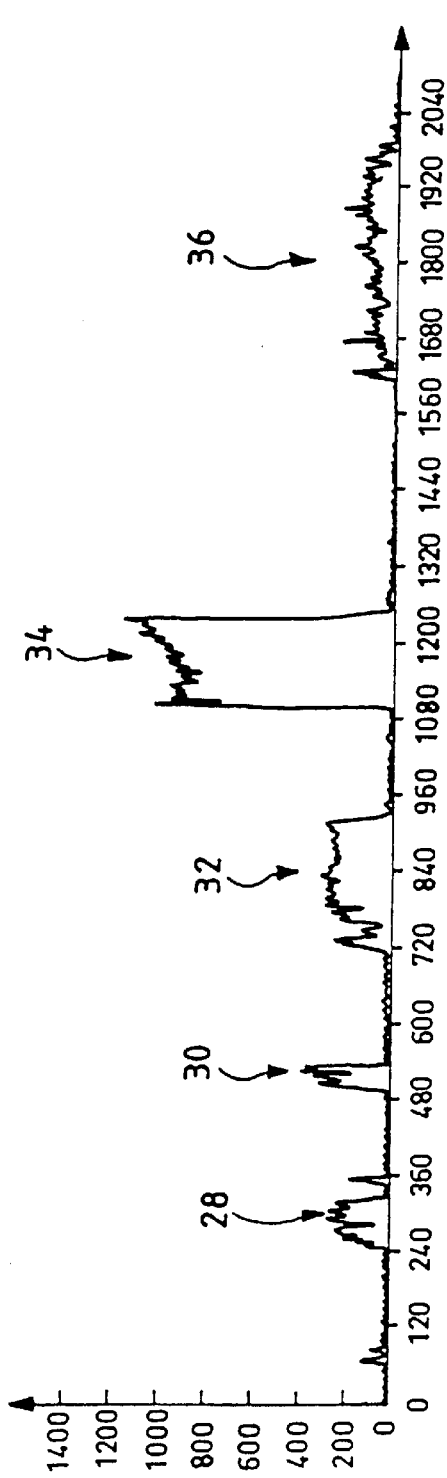
FIG_2
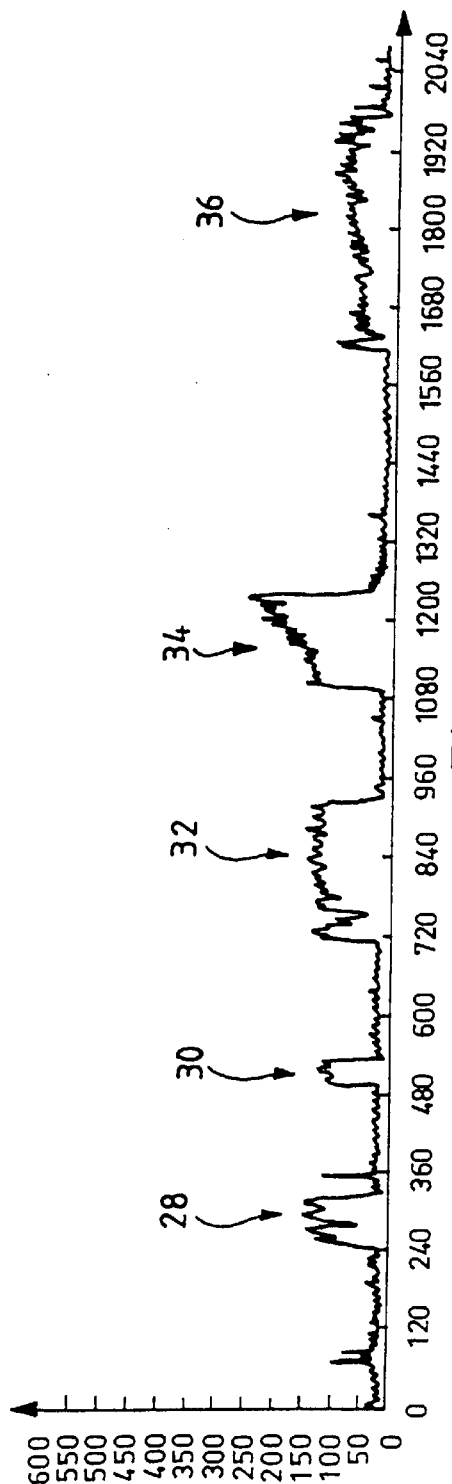
FIG_3

ACTIVE IMPLANTABLE MEDICAL DEVICE ENSLAVED TO A SIGNAL OF ACCELERATION

FIELD OF THE INVENTION

The present invention concerns "active implantable medical devices" such as those defined by the Jun. 20, 1990 Directive 90/385/EEC of the European Community Council, more particularly cardiac pacemakers, cardioverters or defibrillators, whose functioning is enslaved (i.e., responsive) to a parameter detected (or measured) with the help of a sensor. Although the following description refers mainly to the case of a cardiac pacemaker, the invention is applicable in a general manner to a great variety of electronic devices.

BACKGROUND OF THE INVENTION

Implantable active medical devices are known to adapt their actions to the measured or calculated value of a parameter representative of the metabolic needs of the wearer of the device (i.e., the patient in which the device is implanted).

In the case of cardiac pacemakers, these systems compete to increase the frequency of stimulation pulses (the pacing rate) when one detects an increasing activity of the patient bearing the device, and to decrease the stimulation frequency until reaching a base value (a base stimulation rate) in the case of a diminution of the patient's activity, particularly during phases of rest of the patient.

EP-A-0 550 293 and its corresponding U.S. Pat. No. 5,330,510 (each commonly assigned to ELA Medical) describes such a device, where a cardiac pacemaker stimulation frequency is enslaved to a parameter calculated from the measure of an acceleration at the level of the trunk of the patient. The device also is known as a rate responsive pacemaker. U.S. Pat. No. 5,330,510 is incorporated herein by reference in its entirety.

The hypothesis of this device is that the "module" of the acceleration at the level of the trunk of the patient is linked to the activity of the patient. The term "module" refers to a control algorithm that provides a control parameter that is functionally related to the activity level of the patient. Thus, under the module, one increases the stimulation pulse frequency when one detects a growing or increasing activity of the patient, and one decreases the frequency, until a base value is reached, in the case of diminution of the patient activity, and particularly during phases of rest of the patient.

The activity sensor for detecting the patient acceleration preferably comprises one, two or three accelerometers whose axes are perpendicular to each other (respectively called sensors "1D", "2D" or "3D").

In the case of a sensor 1D (a unidirectional accelerometer), the accelerometer is oriented to detect acceleration according to an anterior-posterior axis, that is to say perpendicular to the chest. In the case of a sensor 2D or a sensor 3D, accelerometers are disposed in the pacemaker case (also known as a can or housing) in a manner so that one axis (or two of axes depending on the type of sensor used) is situated in the plane corresponding to the large flat side of the pacemaker case. The pacemaker is then implanted in such a manner that its vertical axis is appreciably parallel to the vertical axis of the patient.

Nevertheless, the pacemaker case is able to turn or displace slightly in the body of the patient, as compared to its initial implanted position, so that the axes of sensors can be found offset in relation to the predetermined reference mark by the vertical axis of the wearer, the lateral axis (corresponding appreciably to the axis of patient's shoulders), and the anterior-posterior axis (perpendicular to the two preceding axes and appreciably perpendicular to the trunk of the patient).

To avoid these variations and displacement of axes, that is to say of the displacement of the mark of the sensor with respect to the reference mark of the patient, the aforementioned EP-A-0 550293 and U.S. Pat. No. 5,350,510 proposes a pacemaker of type sensor 2D or sensor 3D in which the stimulation frequency is enslaved to a module of acceleration signals recorded (detected or measured) on each of the axes. The "module" in this embodiment is defined as the square root of the sum of the squares of the instantaneous amplitude provided by the individual accelerometers on each of the two or three axes; this module is constant in a change of orthogonal references, and it is representative of the whole of acceleration collected by the various accelerometers in the different axes, and, therefore, of the activity of the patient.

Actual practice and clinical studies show, however, that signals sensed by accelerometers are not all representative of a created or applied effort by the patient. As a result, the device measures the module of acceleration signals as a parameter that is not always well correlated to the real effort provided by the patient, and therefore to the metabolic needs or demand of the patient. Thus, one notices that the shocks caused by feet striking the ground produce a peak of acceleration not representative of a patient effort.

For this reason, the signal of acceleration on the vertical axis is larger during the descent of a staircase than during the ascent, while the effort developed by the patient is, on the contrary, more intense during the ascent. Similarly, activities of running, due to the fact of the phenomenon of heel shocks on the ground, are sensed by the vertical sensor in a disproportionate manner in relation to activities of walking.

Conversely, the pedalling of a bicycle, which generates few vibrations, is poorly interpreted, and the enslavement of a function to a parameter of acceleration results in an a undervaluation of the effort actually developed by the patient.

OBJECTS AND SUMMARY OF THE INVENTION

It is, therefore, an object of the invention to avoid this offset in the appreciation of the effort of the patient by suppressing particularly the parasitic signals not representative of the effort in order to minimize, if not eliminate, the influence of these parasites on the enslavement.

Essentially, the solution of the present invention is to apply a limitation to the module of the acceleration, so as to "filter" parasitic acceleration peaks, this limitation being applied only in the detection of an increase, and not in the detection of a decrease. More specifically, the limit is applied to an increase of the square of the instantaneous module of the acceleration in a sensor 2D or sensor 3D.

One aspect of the invention is directed to an improved device of the type generally described in the aforementioned EP-A-0 550 293 and U.S. Pat. No. 5,330,510. One such device comprises a measuring circuit comprising at least one sensor delivering an output signal representative of acceleration, and circuits to deliver, in response to the acceleration signal, a parameter of enslavement of, at least, one function of the device, preferably a cardiac stimulation frequency in the case of a cardiac pacemaker, characterized in that the improvement comprises a means for limiting, in response to a detection of an increasing activity, a value linked to the module of the signal of acceleration.

Advantageously, the limitation is operated on a value proportional to the square of the signal of acceleration, and preferably on a quadratic sum of any individual acceleration components corresponding to distinct axes, respectively delivered by a like plurality of acceleration sensors. Preferably, there are at least two such sensors. In a preferred embodiment, all components of the acceleration signal are sampled in a manner to calculate at each instant a value linked to the module of the acceleration signal. The increase of the value linked to the module of the acceleration signal can then be determined by a comparison between the value associated with the current sample, and the "limited" value associated with the preceding sample. Preferably, the limitation is operated by retaining as the "limited" value either the value associated with the current sample, if the increase is less than a given threshold, or the value retained from the preceding sample which is increased by the value of the threshold, if the increase is greater than the given threshold.

The parameter of enslavement is then preferably an efficient value or an average quadratic of the limited acceleration signal.

BRIEF DESCRIPTION OF THE DRAWINGS

Additional characteristics, features and advantages of the present invention will appear to the person of ordinary skill in the art in view of the following detailed description, made with reference to drawings annexed, in which:

FIGS. 2 and 3 are the chronograms of the parameter of enslavement in various situations of effort, respectively with an enslavement without limitation according to the prior art (FIG. 2), and with an enslavement with limitation according to the invention (FIG. 3).

DETAILED DESCRIPTION OF THE DRAWINGS

Figure 1:
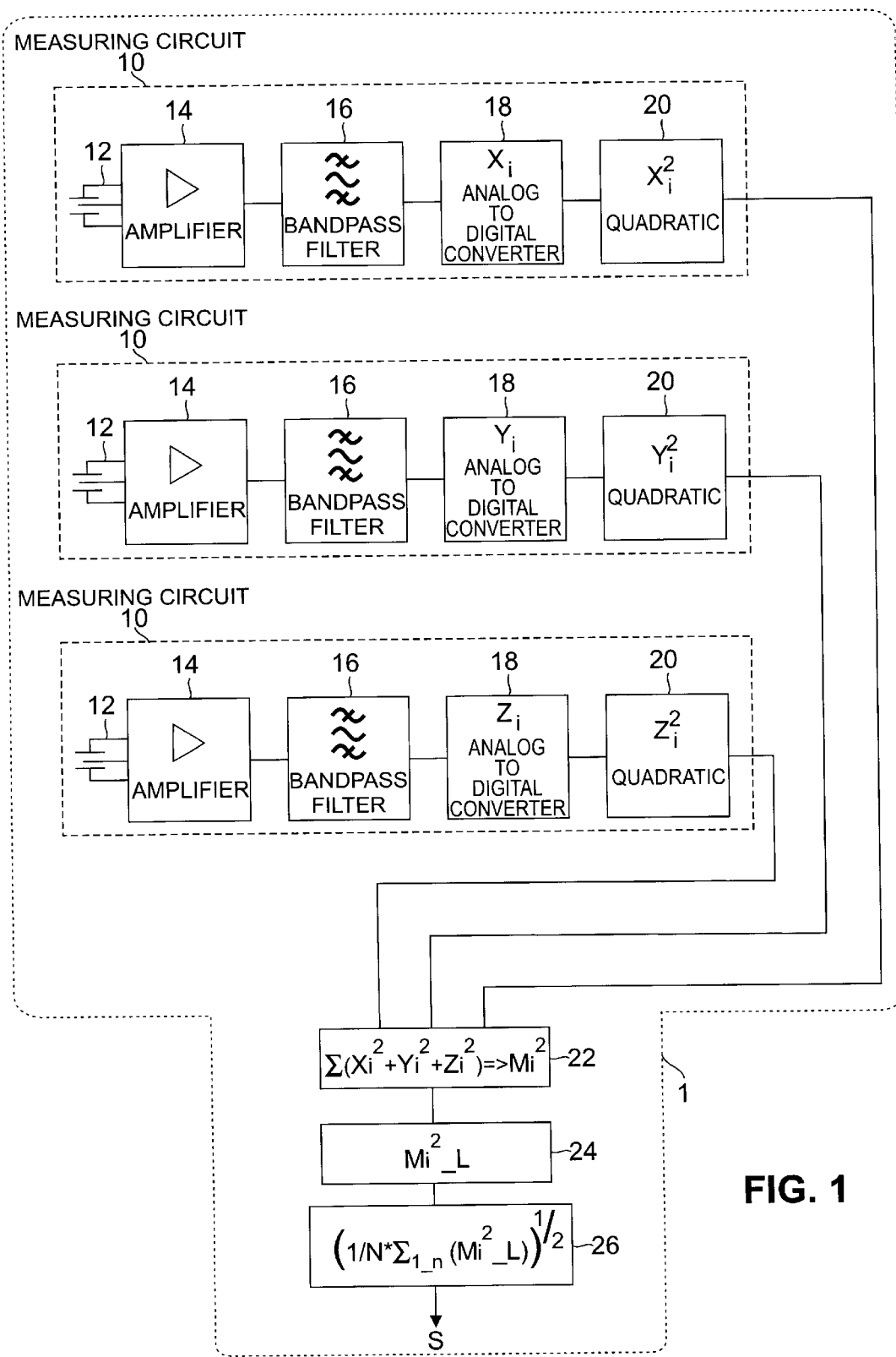
FIG. 1 is a block diagram of a circuit of enslavement implementing an embodiment of the present invention.

Referring to FIG. 1, a block diagram of a circuit 1 able to produce a parameter of enslavement S for an active implantable device, such as a cardiac pacemaker is shown. Although this circuit will be described in the more complex case of an enslavement using a sensor 3D, implying therefore three acceleration measures according to three orthogonal axes X, Y, Z, it should be understood that the invention is not so limited; one also can apply the invention to at least each of the following acceleration sensing devices:

(1) Sensor 1D: the one accelerometer is disposed to detect acceleration along the anterior-posterior axis;

(2) Sensor 2D: the two accelerometers are disposed to detect acceleration along the lateral axis and the vertical axis, and one combines the signals provided by these two accelerometers;

(3) Sensor 3D: either (i) one uses the module of the acceleration as in the example of the following detailed description, or (ii) in an alternate embodiment, one may operate a linear combination of a sensor 1D and a sensor 2D as described above.

In the same manner, the invention will be described in the case of an example where signals are digitally sampled signals, but this example is not in any way restrictive, and the invention is applicable as well to signals sensed and processed by analog circuits.

The circuit of the invention comprises, first of all, three similar measuring circuits 10, respectively, associated with the three acceleration sensors 12 oriented according to three axes X, Y, Z.

These measuring circuits are of a type in themselves known, and one will be able to refer to the detailed description of EP-A-0 550 293 (U.S. Pat. No. 5,330,510) for further details.

Essentially, the signal delivered by each of accelerometers 12, that is, for example, a signal dC of variation of capacity, is applied at a stage 14 for converting variations of capacity to variations of voltage dV, and amplifying the voltage variations.

The signal delivered by the converter and amplifier stage 14 is applied to a band-pass filter 16, to eliminate, on the one hand, parasitic components of high frequencies (the cut-off frequency is typically above 6 Hz) and, on the other hand, the continuous component of gravity (the cut-off frequency is typically below 0.6 Hz).

The filtered signal is then applied to an analog-to-digital converter 18 that samples the signal to give a series of respective, successive samples $X_i$, $Y_i$ and $Z_i$. Typically, the cycle (time of integration) is 1.5625 s, with a frequency of sampling at 20.48 Hz, giving 32 samples per cycle.

The digital signals are then applied to a quadratic stage 20, to give respective squared values $X_i^2$, $Y_i^2$ and $Z_i^2$.

The values $X_i^2$, $Y_i^2$ and $Z_i^2$ are then summed by a stage 22, to give an instantaneous square module $M_i^2 = X_i^2 + Y_i^2 + Z_i^2$.

The instantaneous square module $M_i^2$ is then, in accordance with the present invention, applied to a limiting stage 24 to give an instantaneous limited square module, denoted as $M_i^2\_L$.

This limitation (which can be interpreted as a selective, non linear filtering) is applied only in the detection of an increase of the instantaneous square module.

The function can be preferably implemented by an algorithm in the software controlling a microprocessor based device, and operated in the following manner.

One defines a slope of limitation SLR (for SLew Rate) as a given threshold value, for example, $3906 \times 10^{-6}$ $g^2$ per level (g being representative of the gravitational acceleration), each level corresponding to a sampling step. The threshold is preferably a programmable value. One then compares the instantaneous limited square module of the preceding sample, that is to say $M_{i-1}^2\_L$, to the instantaneous square module of the current sample, that is to say $M_i^2$, and next one applies the rule:

If $M_i^2 - M_{i-1}^2\_L > SLR$, then $M_i^2\_L = M_{i-1}^2\_L + SLR$, otherwise $M_i^2\_L = M_i^2$.

The instantaneous square module limited $M_i^2\_L$ is then applied at a stage 26 to give the parameter of enslavement S, calculated again at each cycle, that is to say every 1.5625 seconds.

Advantageously, the parameter of enslavement S is given by the quadratic average of the N successive samples of the instantaneous square module limited $M_i^2\_L$, that is to say by the quantity:

$$\sqrt{\left(\frac{1}{N} \Sigma_{1 \ldots N} \, M_i^2\_L\right)}$$

One will note that, if one processes analog signals, this quadratic average will correspond to the efficient value of the parameter S(t) over the duration T of the period of integration, namely:

$$\sqrt{(\frac{1}{T}\int_T S^2(t)\,dt)}$$

FIGS. 2 and 3 illustrate, respectively, in the case of a device of the prior art and in the case of a device in accordance with the invention, the evolution of the average module of the acceleration given by an enslavement sensor 2D (that is to say following the lateral and vertical axes) over the course of various phases of patient activities.

These chronograms (with the time in seconds in the abscissa) give in the vertical axis the efficient value of the average module of the acceleration, limited (FIG. 3) and not limited (FIG. 2), expressed in $10^{-6}$ g, g being the value of the gravitational acceleration.

Reported activity phases are indicated as the following:
- at 28: ascending a staircase,
- at 30: descending a staircase,
- at 32: steps (walking),
- at 34: race on foot (running),
- at 36: pedalling.

If one compares FIGS. 2 and 3, one sees that the implementation of the limiting stage of the present invention allows one to obtain a parameter of enslavement S that is larger for a ascending staircase (at region 28) than for descending a staircase (at region 30) which is true according to the physiological reality. In the circuit of the prior art, the indication was the opposite and therefore had a poor correlation with the real metabolic needs of the patient.

Similarly, at region 34, an over-evaluation of the metabolic needs in the case of jogging has been strongly decreased, and it is now closer to that of walking, which, here again, is more physiological and better correlated with the required evolution of the cardiac rhythm and metabolic needs of the patient.

One skilled in the art will appreciate that the present invention can be practiced by other than the aforementioned embodiments, which are presented for purposes of illustration and not of limitation.

I claim:

1. An active implantable medical device capable of functioning in an enslaved mode, said device comprising:
   a measurement circuit comprising at least one sensor responsive to an acceleration and having an acceleration signal representative of said acceleration and a derivation circuit responsive to the acceleration signal for deriving a module of the acceleration signal;
   circuitry for determining, in response to the module of the acceleration signal, a parameter of enslavement (S) of at least one function of the device; and
   means for detecting increases or decrease in the acceleration signal;
   means for limiting the module of the signal of acceleration when an increase in the signal of acceleration is detected by the means for detecting increases or decreases in the acceleration signal, resulting in a limited module of the signal of acceleration.

2. The device of claim 1, further comprising means for deriving a square of the acceleration signal wherein the means for limiting the module of the signal of acceleration utilises the value proportional to the square of the signal of acceleration.

3. The device of claim 2, in which the measurement circuit comprises at least two sensors producing signals representative of acceleration along at least two distinct axes, the device further comprises means for deriving a quadratic sum of individual acceleration components and wherein the means for limiting the module of the signal of acceleration utilises the quadratic sum of individual acceleration components corresponding to said at least two distinct axes.

4. The device of claim 1, further comprising an analog to digital converter in which components of the signal of acceleration are sampled at a predetermined interval in a manner to calculate at each sampling instant an instantaneous square module value ($M_i^2$).

5. The device of claim 4, in which the means for limiting further comprises means for comparing a first instantaneous square module value ($M_i^2$) associated with a current sample and a limited instantaneous square module value ($M_{i-1}^2\_L$) associated with a preceding sample.

6. The device of claim 5, in which the means for limiting further comprises means for retaining the limited value ($M_{i-1}^2\_L$) as the current sample ($M_i^2$) if the increase is less than a programmable threshold (SLR), and as the preceding sample, increased by the the programmable threshold ($M_{i-1}^2\_L+SLR$), if the increase is not less than the threshold.

7. The device of claim 1, in which the parameter of enslavement (S) is one of an efficient value and a quadratic average of the limited module of the signal of the acceleration.

8. The device of claim 1 wherein the function is a stimulation frequency of a cardiac pacemaker.

9. A method of controlling an active implantable medical device having an enslaved function, comprising:
   detecting a signal corresponding to acceleration along at least a first axis;
   determining a module of the signal of acceleration;
   determining an increase in patient activity in response to an increase in said acceleration signal;
   determining a parameter (S) of enslavement of at least one function of the device in response to said determined module; and,
   limiting in response to the determined increase in acceleration, the increase in acceleration signal to said function via the module.

10. The method of claim 9, in which the limiting step comprises determining a limiting value proportional to a square of the signal of acceleration.

11. The method of claim 10, wherein the step of detecting a signal corresponding to acceleration comprises detecting individual signals corresponding to acceleration components detected on at least two perpendicular axes and in which the limiting step comprises calculating a quadratic sum of individual acceleration components according to said at least two axes.

12. The method of claim 9, further comprising sampling the signal of acceleration and calculating at each sampling an instantaneous square module value ($M_i^2$).

13. The method of claim 12, in which the limiting step further comprises comparing the value ($M_i^2$) associated with a current sample to a limited value associated with a preceding sample ($M_{i-1}^2$).

14. The method of claim 13, in which the limiting step further comprises determining the limited value as the value ($M_i^2$) associated with the current sample if the increase in acceleration is less than a programmable threshold (SLR), and determining the limited value as the value associated with the preceding sample ($M_{i-1}^2$) increased by the threshold if the increase in acceleration is not less than the threshold.

15. The method of claim 9, further comprising providing the parameter of enslavement (S) as one of an efficient value and a quadratic average of the limited signal of acceleration.

16. A cardiac pacemaker having a cardiac stimulation frequency enslaved to acceleration limited according to the method of any of claims 9, 10, 11, 12, 13, 14 or 15.

17. A pacemaker having a controllable stimulation frequency controlled by a control parameter related to the patient's effort, comprising:

a pacemaker box having a flat surface for implanting in a vertical orientation in a patient;

first means for measuring a first signal corresponding to an acceleration due to patient effort along a first axis;

second means for measuring a second signal corresponding to acceleration due to patient effort along a second axis, wherein the first and second axes are perpendicular to one another and parallel to said flat surface of the pacemaker box;

means for providing a module of a signal of acceleration from the first and second signals;

means for computing the control parameter for controlling the stimulation frequency based on the first and second signals;

means for detecting an increase in said first and said second acceleration signals; and means for limiting a value utilized in providing the module of the signal of acceleration in response to the detected increase in acceleration signals.

18. In a pacemaker having a controllable stimulation frequency, a method for providing a control parameter related to the effort of a patient, comprising the steps of:

providing a pacemaker box with a flat surface for implantation in a patient so that said surface is disposed in a vertical orientation;

measuring first and second signals corresponding to acceleration caused by patient effort, along first and second axes which are perpendicular to one another and parallel to said flat surface of the pacemaker box;

providing a module of a signal of acceleration from the first and second signals;

computing the control parameter based on the first and second signals; and providing said control parameter for controlling the pacemaker stimulation frequency;

determining an increasing acceleration; and limiting a value utilized in providing the module of the signal of acceleration in response to said determined increase in acceleration.

19. A method for calculating a control parameter related to a patient's effort for use in controlling a stimulation frequency of a pacemaker comprising:

a) measuring first and second signals corresponding to the acceleration along first and second axes which are perpendicular to one another;

b) providing a sum of absolute values of the first and second signals as a third signal; and c) integrating the third signal over a time period and providing said integrated third signal as the control parameter used to control the stimulation frequency of the pacemaker;

d) determining an increase in acceleration via said first and said second signals; and e) limiting the third signal in response to the determined increase in acceleration.

* * * * *